(12) United States Patent
Adachi et al.

(10) Patent No.: US 6,215,844 B1
(45) Date of Patent: Apr. 10, 2001

(54) X-RAY COMPUTED TOMOGRAPHY APPARATUS

(75) Inventors: Akira Adachi, Otawara; Toshihiro Rifu, Nasu-gun, both of (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/366,753

(22) Filed: Aug. 4, 1999

(30) Foreign Application Priority Data

Aug. 6, 1998 (JP) .................................................. 10-222745
Aug. 11, 1998 (JP) .................................................. 10-227316

(51) Int. Cl.⁷ ....................................................... A61B 6/00
(52) U.S. Cl. ............................................. 378/19; 378/205
(58) Field of Search ............................... 378/4, 9, 20, 15, 378/205, 207

(56) References Cited

U.S. PATENT DOCUMENTS 5,566,220   10/1996   Saito et al. .

5,583,903  * 12/1996   Saito et al. .............................. 378/19

FOREIGN PATENT DOCUMENTS 3-109054    5/1991   (JP) .
9-285462   11/1997   (JP) .

* cited by examiner

Primary Examiner—David P. Porta
(74) Attorney, Agent, or Firm—Oblon, Spivak, McClelland, Maier & Neustadt, P.C.

(57) ABSTRACT

In an X-ray computed tomography apparatus, an X-ray tube for generating an X-ray is opposed to a main X-ray detector in order to acquire a projection data set necessary to reconstruct a tomogram. A first sub X-ray detector is arranged at the righthand of the main X-ray detector. A second sub X-ray detector is arranged at the lefthand of the main X-ray detector. Arranging the sub X-ray detectors adjacent to the respective opposite sides of the main X-ray detector enables accurate detection of the shift of an X-ray radiation field, and hence enables the reduction of errors due to the shift.

21 Claims, 8 Drawing Sheets

X-RAY COMPUTED TOMOGRAPHY APPARATUS

BACKGROUND OF THE INVENTION

This invention relates to an X-ray computed tomography apparatus for reconstructing tomogram data on the basis of a set of projection data concerning a to-be-examined subject.

Figure 1:
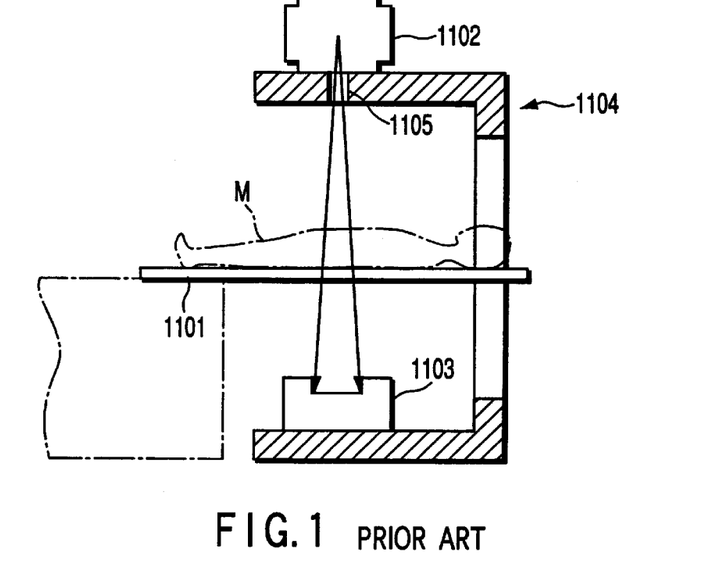
FIG. 1 is a side view illustrating a gantry incorporated in a conventional X-ray computed tomography apparatus.

FIG. 1 is a side view illustrating a gantry incorporated in a conventional X-ray computed tomography apparatus. X-rays are generated by an X-ray tube 1102. The X-rays are shaped in the form of a fan by an X-ray collimator 1105. The shaped X-rays pass through a to-be-examined subject M placed on a table 1101. The passed X-rays are detected by an X-ray detector 1103. The X-ray tube 1102 and the X-ray detector 1103 are fixed on a rotary frame 1104. While the rotary frame 1104 rotates, an x-ray detecting operation is repeated, thereby collecting a projection data set necessary for reconstructing tomogram data of one frame.

Figure 2A:
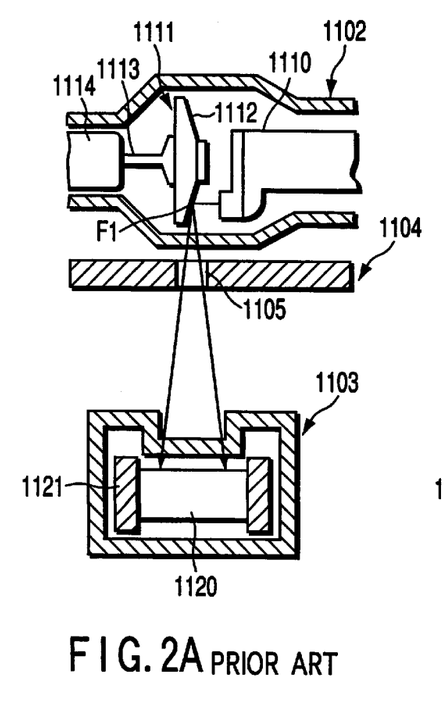
FIG. 2A is a side view, illustrating an X-ray radiation field assumed when in the conventional case, an X-ray focus is situated in a predetermined position.

Ion chamber type and semiconductor type X-ray detectors 1103 are available. FIG. 2A shows the ion chamber type X-ray detector 1103. This X-ray detector 1103 comprises an ion chamber sealing Xe gas therein, a plurality of electrode plates 1120 arrayed parallel in the ion chamber, and insulating plates 1121 made of, for example, ceramic and holding the electrode plates 1120.

The principle of detection will be described. When X-rays have entered a space between each pair of adjacent electrode plates 1120, electrons and electron holes generated by the ionization power of the X-rays are attracted by each pair of electron plates 1120 supplied with a voltage, respectively, thereby generating a signal current corresponding to the intensity of the X-rays. Each pair of adjacent electrode plates 1120 constitutes one channel or detector element.

The direction in which the detector elements are arranged will be hereinafter referred to as a "channel direction", and a direction perpendicular to the channel direction and parallel to the axis-of-rotation of the rotary frame 1104 will be referred to as a "slice direction".

The semiconductor type X-ray detector 1103 comprises a plurality of X-ray detector elements, each of which consists of a semiconductor layer, a voltage applying electrode provided on one surface of the semiconductor layer, and a signal electrode provided on the reverse surface of the semiconductor layer. The principle of detection is basically the same as that of the ion chamber type X-ray detector. Further, there may be a case where an element consisting of a scintillator and a photodiode is used as an X-ray detector element.

The X-ray tube 1102 is mainly of a rotary anode type, in which a rotary anode is employed. As is shown in FIG. 2A, thermoelectrons emitted from a cathode 1110 are accelerated and applied onto a target 1112 incorporated in a rotary anode 1111, thereby generating X-rays. The target 1112 will be hereinafter referred to as an "X-ray focus". Further, the position (home position) of an X-ray focus F at an ordinary temperature will be represented by F1.

Figure 2B:
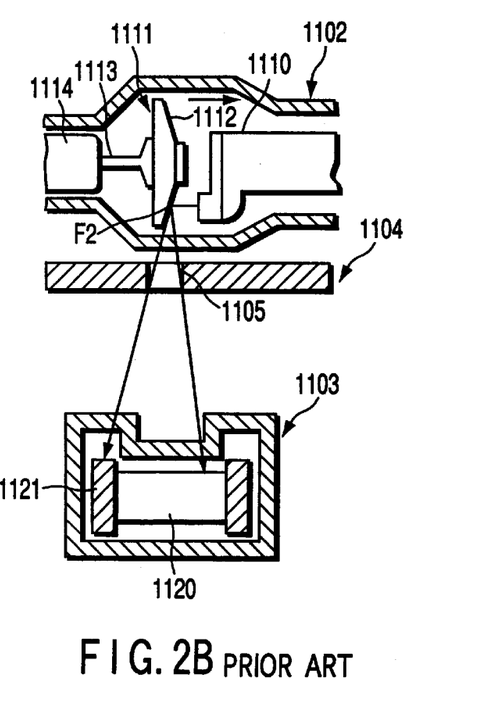
FIG. 2B is a side view, illustrating an X-ray radiation field assumed when in the conventional case, the X-ray focus is situated in a position shifted from the predetermined position due to thermal expansion.

As is well known, the conversion efficiency of X-ray energy to electric energy is less than 1 percent. Not less than 99% of electric energy is converted into heat energy. The internal temperature of the X-ray tube 1102 reaches a significantly high temperature, and therefore the rotation axis 1113 and a bearing 1114 incorporated in the rotary anode 1111 thermally expand. As a result, the X-ray focus shifts from the predetermined position F1. Where the X-ray focus is situated in a shifted position F2, the range of the detector 1103 on which X-rays strike, i.e. the X-ray radiation field, differs from that of a case where the X-ray focus is situated in the predetermined position F1 (see FIGS. 2A and 2B). Accordingly, an error occurs in the output of the detector. The output error causes a ring artifact in a tomogram. The change of the X-ray radiation field will be caused by various factors such as an attachment error of the X-ray detector to the rotary frame, an operation error of the collimator, warping/deformation of the upper slit or the detector due to the high speed rotation of the rotary frame, etc., as well as a shift of the X-ray focus.

Japanese Patent Application KOKAI Publications Nos. 6-269443, 3-109054 and 9-285462 disclose methods for reducing the above-described disadvantages. Specifically, they disclose a technique for correcting a set of projection data using a computer, or for mechanically sliding the X-ray tube and/or the X-ray detector in a direction opposite to the shift direction of the radiation field, on the basis of the relationship between the shift distance of the radiation field (or a temperature increase) measured in advance, and a change in detection sensitivity, and also on the basis of the actual shift distance of the radiation field when photographing.

However, since in the above technique, only the shift distance of the radiation field in the channel direction is measured, the correction accuracy is low. In other words, the shift of the radiation field in the slice direction and/or the slant of the center line of the radiation field with respect to the center line of the detection field cannot be corrected. This means, in particular, that even if this technique is directly applied to multi-slice detectors, the use of which has significantly increased recently, the correction accuracy is kept extremely low. There is another conventional apparatus, in which X-rays are radiated in a wide range so that the entire surface of the detector can be radiated with the X-rays irrespective of the position of the X-ray focus. This structure, however, inevitably increases the amount of X-ray radiation on a to-be-examined subject.

Specifically, different from the single-slice detector that uses only a substantially flat detector section through a beam trimmer, the multi-slice detector includes individually separated fluorescent substances, and has a sensitivity distribution in the form of an arc. Where the application of X-rays differs between the time of scanning and the time of calibration, the probability of occurrence of a ring artifact is significantly high in the multi-slice detector than in the single-slice detector. Since in the case of the multi-slice detector, the arc-shaped sensitivity distribution exists in both the channel direction and the slice direction, it is necessary to two-dimensionally measure X-rays applied to the detector and to select correction data.

In addition, to correct the shift of the radiation field, the X-ray tube and/or the X-ray detector is slid as mentioned above. Since, however, this X-ray tube and detector are very heavy, they cannot be positioned with high accuracy.

BRIEF SUMMARY OF THE INVENTION

It is the object of the invention to provide an X-ray computed tomography apparatus equipped with a multi-slice X-ray detector, which is capable of accurately reducing errors due to the shift of its X-ray radiation field.

In an X-ray computed tomography apparatus of the invention, an X-ray tube for generating an X-ray is opposed to a main X-ray detector in order to acquire a projection data set necessary to reconstruct a tomogram. Further, a first sub X-ray detector is arranged at the righthand of the main X-ray detector, and a second sub X-ray detector is arranged at the lefthand of the main X-ray detector. Arranging the sub X-ray detectors adjacent to the respective opposite sides of the main X-ray detector enables accurate detection of the shift of an X-ray radiation field, and hence enables the reduction of errors due to the shift.

In an X-ray computed tomography apparatus of the invention, an X-ray tube for generating an X-ray is opposed to a main X-ray detector in order to acquire a projection data set necessary to reconstruct a tomogram. Further, to accurately detect the shift of an X-ray radiation field, a first sub X-ray detector is arranged at the righthand of the main X-ray detector, and a second sub X-ray detector is arranged at the lefthand of the main X-ray detector. To correct the shift of the X-ray radiation field, an X-ray collimator is slid in accordance with the detected shift of the X-ray radiation field. Since the X-ray collimator is lighter than the X-ray tube or the main X-ray detector, it can be positioned with higher accuracy.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

The preferred Embodiments of the invention will be described in detail with reference to the accompanying drawings.

First Embodiment

Figure 3:
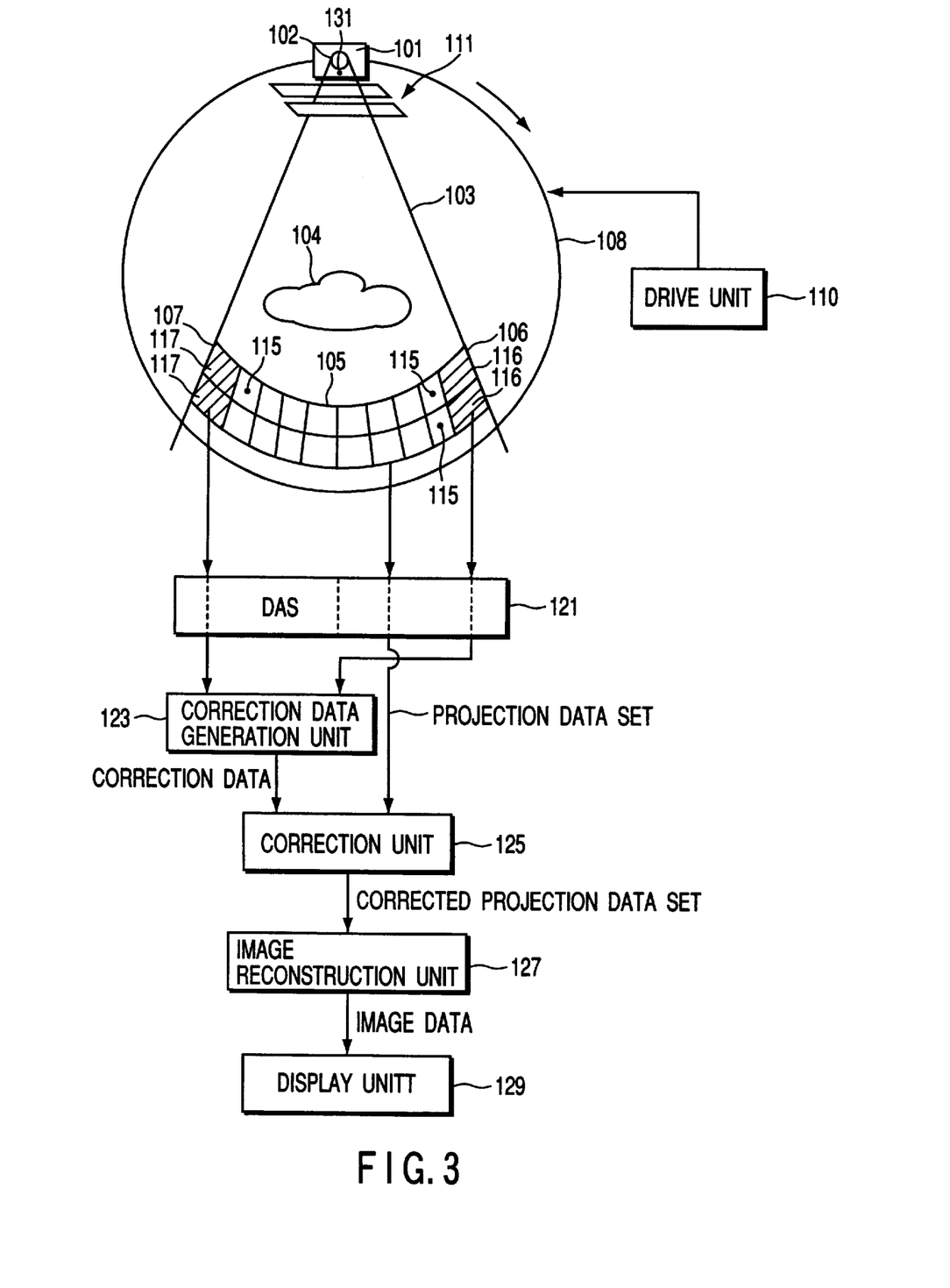
FIG. 3 is a schematic view illustrating the structure of an X-ray computed tomography apparatus according to a first embodiment of the invention.

FIG. 3 shows the structure of an X-ray computed tomography apparatus according to a first embodiment of the invention. An X-ray tube 101 is of a rotary anode type in which a rotary anode is employed. When thermoelectrons emitted from a cathode and accelerated have been applied to a target (X-ray focus) 102 incorporated in the rotary anode, an X-ray is generated at the X-ray focus 102, and output through an X-ray radiation window 131. The position (home position) of the X-ray focus 102 at an ordinary temperature will be represented by F1. An X-ray collimator 111 is attached to the window 131 for shaping an X-ray in the form of a fan. The collimator 111 is of a slit movable type, in which the width, slice-directional position and slant angle of a slit are variable.

A main X-ray detector 105 is opposed to the X-ray tube 101 and the collimator 111, with a to-be-examined subject M interposed therebetween. Further, sub X-ray detectors 106 and 107 are opposed to the X-ray tube 101 and the collimator 111 without interposing the to-be-examined subject M therebetween.

Figure 4:
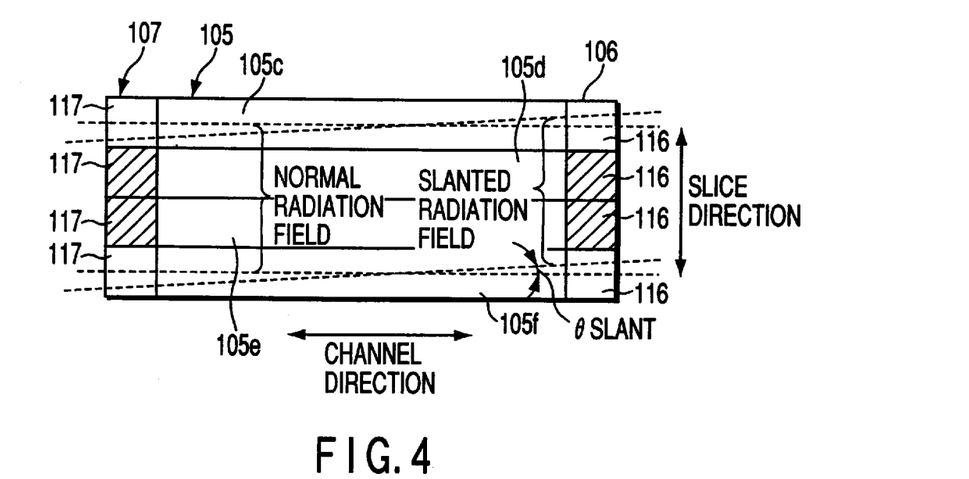
FIG. 4 is a plan view showing a main X-ray detector and a sub X-ray detector incorporated in the apparatus of FIG. 3.

FIG. 4 is a plan view of the main X-ray detector 105 and the sub X-ray detectors 106 and 107. The main X-ray detector 105 is adapted to a multi-slice function, and has a plurality of X-ray detector element rows 105c, 105d, 105e and 105f arranged parallel to each other in the slice direction. Each X-ray detector element row consists of an ion chamber row or a semiconductor element row. Moreover, each X-ray detector element row includes a plurality of X-ray detector elements 115 arrayed in the channel direction.

The sub X-ray detector 106 is arranged at the righthand of the main X-ray detector 105 in the channel direction. The other sub X-ray detector 107 is arranged at the left-hand of the main X-ray detector 105 in the channel direction. In other words, the main X-ray detector 105 is located between the sub X-ray detectors 106 and 107. In this arrangement, a greater part (which constitutes a central portion of a fan-shaped X-ray) of an X-ray generated by the X-ray tube 101 and shaped by the collimator 111 passes through the to-be-examined subject M placed on the table and enters the main X-ray detector 105. The remaining portions (which constitute both opposite portions of the fan-shaped X-ray) of the X-ray pass either side of the subject M and are detected by the sub X-ray detectors 106 and 107.

The sub X-ray detector 106 has a plurality of X-ray detector elements 116 arrayed in the slice direction. Similarly, the sub X-ray detector 107 has a plurality of X-ray detector elements 117 arrayed in the slice direction. Typically, the number of the X-ray detector elements 116 of the sub X-ray detector 106 is identical to that of the rows of the main X-ray detector 105. Similarly, the number of the X-ray detector elements 117 of the sub X-ray detector 107 is identical to that of the rows of the main X-ray detector 105. However, the number of the X-ray detector elements 116 of the sub X-ray detector 106 may differ from that of the rows of the main X-ray detector 105, and the number of the X-ray detector elements 117 of the sub X-ray detector 107 may differ from that of the rows of the main X-ray detector 105. More typically, the number of the X-ray detector elements 116 of the sub X-ray detector 106 is identical to that of the X-ray detector elements 117 of the sub X-ray detector 107, but they may differ from each other.

Figure 5A:
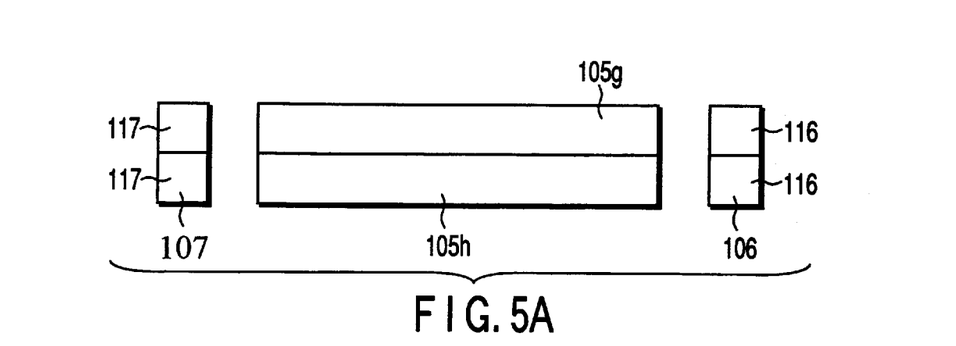
FIG. 5A is a plan view showing a main X-ray detector and a sub X-ray detector incorporated in the apparatus of FIG. 3.

As is shown in FIG. 5A, it suffices if the main X-ray detector 105 has at least two X-ray detector element rows 105g and 105h, and accordingly each sub X-ray detector 106 or 107 has at least two detector elements 116 or 117.

Typically, the sub X-ray detectors 106 and 107 are located in contact with the right and left sides of the main X-ray detector 105, respectively. However, each of the sub X-ray detectors 106 and 107 may be separated by a predetermined distance from the main X-ray detector 105.

Also typically, the X-ray detector elements 116 of the sub X-ray detector 106 are the same type detector elements as the detector elements 115 of the main X-ray detector 105. Similarly, the X-ray detector elements 117 of the sub X-ray detector 107 are of the same type as the detector elements 115 of the main X-ray detector 105. The X-ray detector elements 116 and 117 of the sub X-ray detectors 106 and 107, however, may be formed of different type detector elements from those of the main X-ray detector 105.

Still typically, a central portion of an X-ray detector as one body is used as the main X-ray detector 105, and opposite end portions thereof are used as the sub X-ray detectors 106 and 107. However, the main X-ray detector 105 and the sub X-ray detectors 106 and 107 may be formed of separate bodies and assembled into one body.

Figure 5B:
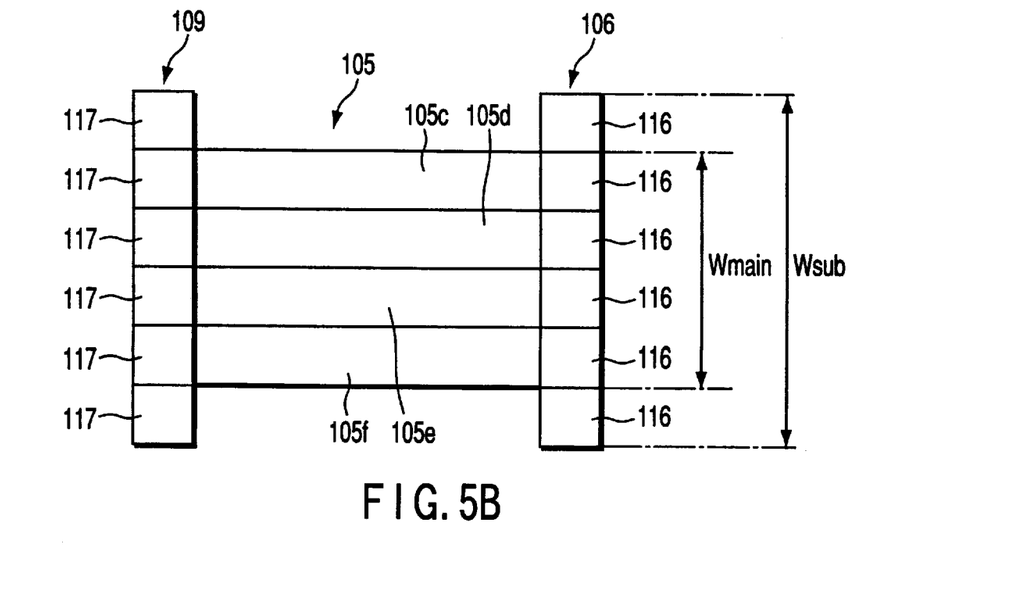
FIG. 5B is a plan view showing a main X-ray detector and a sub X-ray detector incorporated in the apparatus of FIG. 3.

Yet typically, the entire slice-directional width Wsub of the sub X-ray detectors 106 and 107 is substantially the same as the entire slice-directional width Wmain of the main X-ray detector 105. However, as shown in FIG. 5B, the entire slice-directional width Wsub of the sub X-ray detectors 106 and 107 may be greater than the entire slice-directional width Wmain of the main X-ray detector 105. When the entire slice-directional width Wsub is greater than the entire slice-directional width Wmain, the range of detection in which the amounts of shift and slant of the X-ray radiation field can be detected is wider than the case where the entire slice-directional width Wsub is substantially the same as the entire slice-directional width Wmain.

The X-ray tube 101, the main X-ray detector 105 and the sub X-ray detectors 106 and 107 are fixed on a rotary frame 108. While the rotary frame 108 is rotated by a drive unit 110, an X-ray detection operation is repeated. As a result, a projection data set necessary for the reconstruction of tomogram data of one frame, i.e. a data set for 360° or (180°+α)(α indicates the angle of the fan beam), is collected in a data acquisition system (DAS) 121 via the main X-ray detector 105. Similarly, the data output from the sub X-ray detectors 106 and 107 is collected in the data acquisition system 121.

Figure 6:
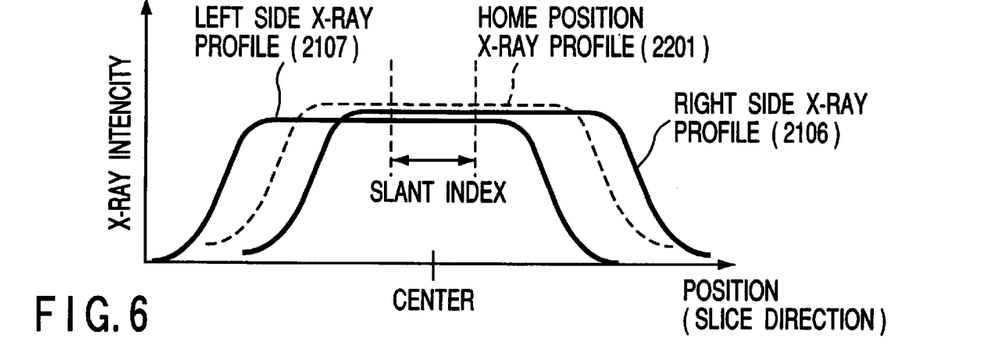
FIG. 6 is a view illustrating X-ray profiles obtained when X-rays have entered righthand and lefthand sub detectors where the X-ray radiation field slants.

The output data of the sub X-ray detectors 106 and 107 indicates the shift of the X-ray radiation field due to, for example, the shift of the X-ray focus, i.e. the shift distance of the X-ray radiation field in the channel direction, and also indicates the slant angle of the center line of the X-ray radiation field to the center line of the main X-ray detector 105. FIG. 6 shows the slice-directional profile 2106 of an X-ray entering the sub detector 106, and the slice-directional profile 2107 of an X-ray entering the sub detector 107, when the X-ray radiation field is slant (see FIG. 4). It is a matter of course that output data profiles obtained by arranging the output data of the sub detectors 106 and 107 in the slice direction reflect the X-ray profiles 2106 and 2107. The slant angle $\theta_{slant}$ of the X-ray radiation field corresponds to a spatial deviation (slant index) between the righthand X-ray profile 2106 and the left-hand X-ray profile 2107.

Figure 7:
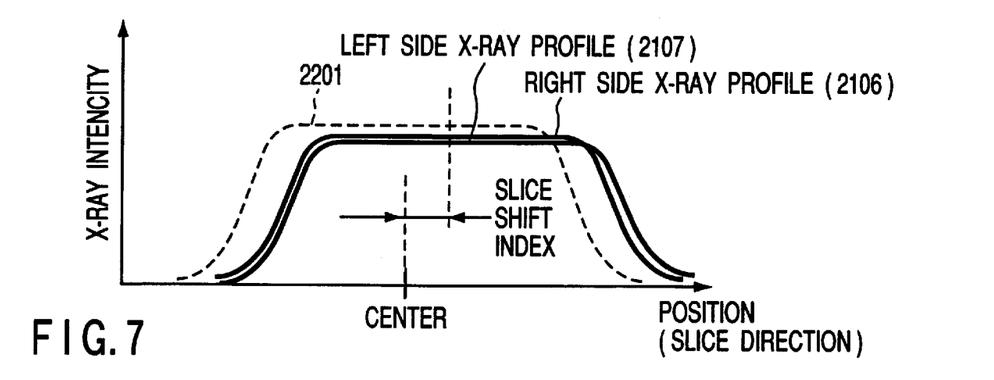
FIG. 7 is a view illustrating X-ray profiles obtained when X-rays have entered the righthand and lefthand sub detectors where the X-ray radiation field has shifted.

FIG. 7 shows the slice-directional profile 2106 of an X-ray entering the sub detector 106, and the slice-directional profile 2107 of an X-ray entering the sub detector 107, when the X-ray radiation field shifts in the slice direction. The slant angle $\theta_{slant}$ of the X-ray radiation field corresponds to a spatial deviation (slice shift index) between the righthand X-ray profile 2106 and the left-hand X-ray profile 2107.

The shift distance of the X-ray radiation field in the channel direction can be measured based on the output difference (channel shift index) between the sub detectors 106 and 107, as in the conventional case.

A correction data generation unit 123 generates correction data for removing the influence of the shift of the X-ray radiation field due to, for example, the shift of the X-ray focus, on the basis of the output data of the sub X-ray detector 106 supplied from the data acquisition system 121. The correction data may be acquired in advance for each of various shift/slant patterns of the X-ray radiation field, stored in an internal memory, and selectively read therefrom in accordance with the output data of the sub X-ray detector 106 obtained at the time of actual photographing. Alternatively, the correction data may be calculated using a predetermined formula and the output data of the sub X-ray detector 106 obtained at the time of actual photographing. If suffices if the correction data is collected with a certain pitch in a direction parallel to the slice direction, using the tracking collimator with the upper slit. Further, the correction data, which is ideally indicated by a slant linear line, is actually obtained as approximate correction data in each channel from data indicated by a stepped line.

A correction unit 125 corrects the projection data set from the data acquisition system 121 on the basis of correction data generated by the correction data generation unit 123. On the basis of the corrected projection data set, tomogram data is reconstructed by an image reconstructing unit 127. A tomogram corresponding to the tomogram data is displayed on a display 129.

Figure 8:
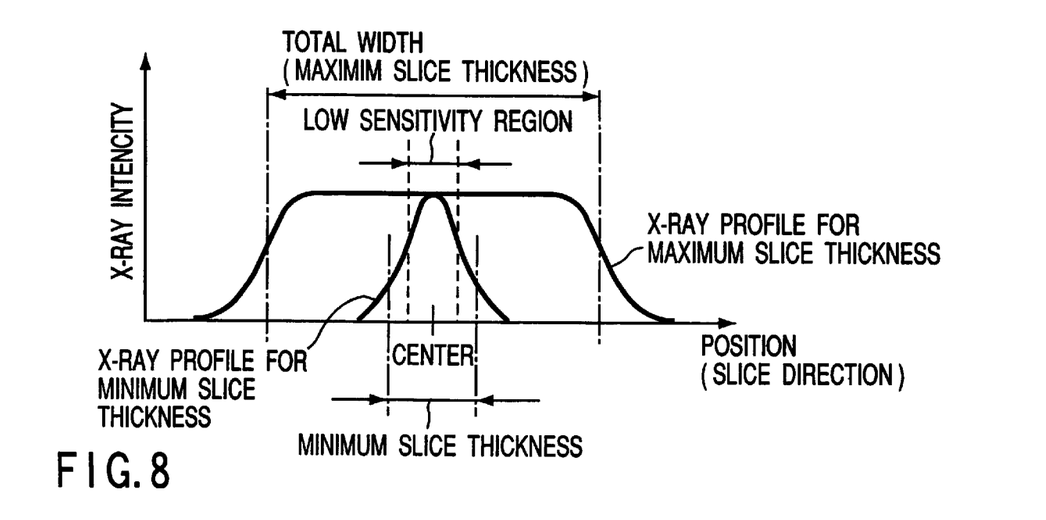
FIG. 8 is a view illustrating an X-ray profile corresponding to a maximum slice thickness, and an X-ray profile corresponding to a minimum slice thickness.

It should be noted that the X-ray radiation field does not shift or slant limitlessly. The X-ray radiation field shifts and/or slants within a certain range. Further, as is shown in FIG. 8, a central portion of the slice-directional X-ray profile is a flat umbra portion, while the opposite side portions are half shadow portions. Accordingly, even if the X-ray radiation field shifts by the maximum distance or slants by the maximum angle, the flat umbra portion of the X-ray is applied to the detector elements 116 and 117 arranged at the respective slice-directional centers of the sub detectors 106 and 107 and their vicinities. In other words, the output data of the detector elements 116 and 117 (hatched ones in FIG. 4) arranged at the slice-directional centers of the sub detectors 106 and 107 and their vicinities contains a DC component, and no data difference can be obtained from the detector elements arranged at the slice-directional centers and their vicinities.

Therefore, there is no actual influence upon the calculation of the shift of the X-ray radiation field, even if the detector elements 116 and 117 arranged at the respective slice-directional centers of the sub detectors 106 and 107 and their vicinities are made to have low or no sensitivity, or even if no detector elements are provided at the slice-directional centers of the sub detectors 106 and 107 and their vicinities, in order to avoid a state in which the output data of the detector elements 116 and 117 arranged at the slice-directional centers of the sub detectors 106 and 107 and their vicinities converts into noise. It is a matter of course that even when photographing the minimum slice thickness area, reduction of sensitivity should be done in an area narrower than the minimum slice thickness area, so that shift of the X-ray radiation field can be detected.

The reduction of sensitivity can be performed by various methods. For example, the sensitivity of the X-ray detector elements 116 and 117 arranged at the slice-directional centers of the sub detectors 106 and 107 and their vicinities can be made lower than that of the X-ray detector elements 116 and 117 arranged in slice-directionally peripheral areas of the sub detectors 106 and 107 by reducing the thickness (ionization distance) of the elements arranged at the respective centers and their vicinities, to about $2/3$–$1/3$ of the elements arranged in the peripheral areas.

There is another method, in which the sensitivity of the X-ray detector elements 116 and 117 arranged at the slice-directional centers of the sub detectors 106 and 107 and their vicinities can be made lower than that of the X-ray detector elements 116 and 117 arranged in slice-directionally peripheral areas of the sub detectors 106 and 107, or can be made substantially zero, by covering the elements arranged at the respective centers and their vicinities, with a member having an appropriate X-ray absorbing coefficient, for example, an X-ray filter made of a heavy metal such as lead or its alloy.

Where each detector element is formed of a scintillator and a photodiode, the sensitivity of the X-ray detector elements 116 and 117 arranged at the respective slice-directional centers and their vicinities can be made lower than that of the X-ray detector elements 116 and 117 arranged in slice-directionally peripheral areas, or can be made substantially zero, by inserting an optical filer formed of, for example, a translucent or opaque resin plate, between the scintillator and the photodiode of each of only the detector elements arranged at the respective centers and their vicinities. Further, there is a method in which the sensitivity of the sub detector 106 or 107 can be made substantially zero at the slice-directional center thereof and its vicinity by providing no detector elements there.

There is yet another method in which the sensitivity of the X-ray detector elements 116 and 117 arranged at the respective slice-directional centers and their vicinities can be made lower than that of the X-ray detector elements 116 and 117 arranged in respective slice-directionally peripheral areas, or can be made substantially zero, by acquiring no signals output from the X-ray detector elements 116 and 117 arranged at the respective slice-directional centers and their vicinities, by outputting no signals corresponding thereto from the data acquisition system 121, or by making the amplification factor of the output signals of the X-ray detector elements 116 and 117 arranged at the respective slice-directional centers and their vicinities, lower than that of the other X-ray detector elements.

A correction method for use in the X-ray computed tomography apparatus of the embodiment will now be described.

First, a description will be given of a method for collecting correction data. This method is basically similar to the conventional one. Correction is performed by multiplying the output signal of each detector element by a correction coefficient. There is provided one set of correction coefficients corresponding to respective detector elements. Correction data includes a plurality of sets of correction coefficients. The number of the correction coefficient sets is identical to the number of patterns obtained by multiplying the number of views (the number of samples per one rotation of the X-ray tube 101) by the shift/slant of the X-ray radiation field (shift distance, slant angle). In other words, one correction coefficient is determined using one X-ray radiation field shift/slant pattern, one view number (indicative of the rotational angle of the X-ray tube 101) and one row number.

The correction data is obtained based on a projection data set which is acquired by scanning, in a manner similar to the actual manner, a cylindrical phantom of a uniform X-ray absorption coefficient. Alternatively, the correction data is obtained based on a projection data set which is acquired by moving the slit of the movable X-ray collimator 111 while emitting an X-ray, so as to reproduce the actual scan operation.

The collection of correction data using the movable collimator 111 is actually performed as follows: First, the slit of the collimator 111 is slightly moved and/or rotated so that the X-ray radiation field can slightly move from its home position in the slice direction and/or slightly slant. This operation is intermittently repeated until the shift distance and slant angle of the X-ray radiation field reach their respective maximum values. During the operation, data collection is repeated. The correction data is obtained on the basis of the collected projection data set. In other words, a correction coefficient that can make all data items have the same value is obtained.

Figure 9:
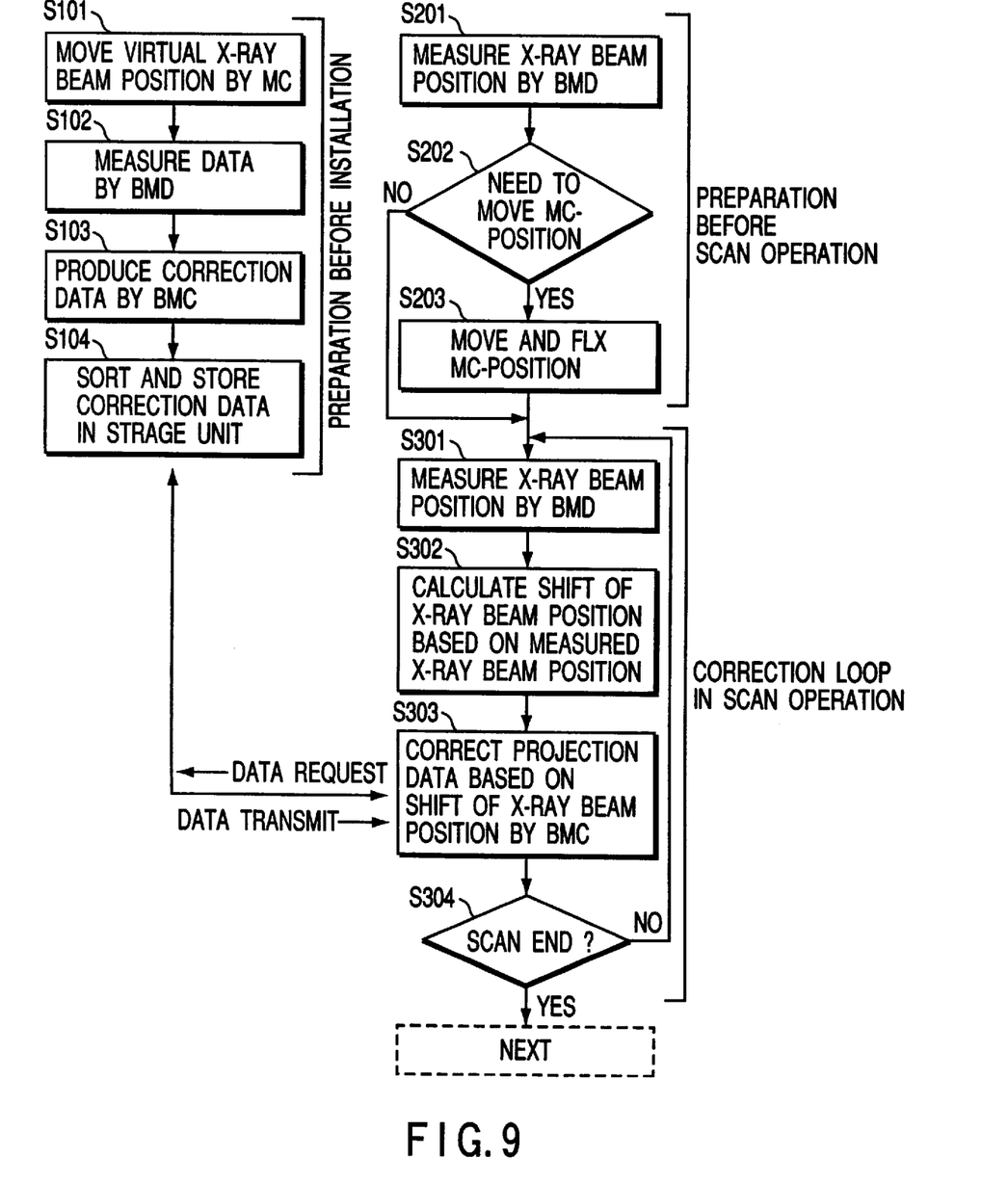
FIG. 9 is a flowchart useful in explaining the operation of the X-ray computed tomography apparatus according to the first embodiment of the invention.

FIG. 9 illustrates the procedure of the correction operation. First, correction data is obtained at a preparation stage before the installment of the apparatus. At a step S101, the slit of the movable collimator 111 is moved/rotated by the drive unit 110, thereby slice-directionally shifting and/or slanting the X-ray radiation field. Each time the X-ray radiation field is moved/rotated, data is acquired by the DAS 121 via the main detector 105 and the sub detectors 106 and 107. At a step S103, on the basis of the acquired data, one correction coefficient is calculated by the correction data generation unit 123 for each shift/slant pattern of the X-ray radiation field, each view number and each row number. At a step S104, the calculated correction coefficients are stored as correction data in the correction data generation unit 123 in relation to each shift/slant pattern of the X-ray radiation field, each view number and each row number.

Then, the X-ray tube 101 is warmed up in a preparation operation before a scanning operation, followed by a step S201 where the shift/slant pattern of the X-ray radiation field is calculated on the basis of the outputs of the sub detectors 106 and 107. When the amount of shift/slant exceeds an allowable range, the slit of the collimator III is moved (steps S202 and S203).

In the scan operation period, correction data corresponding to the outputs (indicative of the shift/slant pattern) of the sub detectors 106 and 107 are read from the memory at steps S301, S302 and S303, thereby correcting the projection data set acquired by the main detector 105, using the correction data. The same data acquisition and correction operation is repeated till the last view (step S304). Although the correction operation is performed at each view, it may be performed at every n-th view (n: positive integer).

In this embodiment, at least one of the slice-directional shift and the slant of the X-ray radiation field can be detected as well as the channel-directional shift thereof. Accordingly, the projection data set can be corrected with significantly high accuracy.

Second Embodiment

Figure 10:
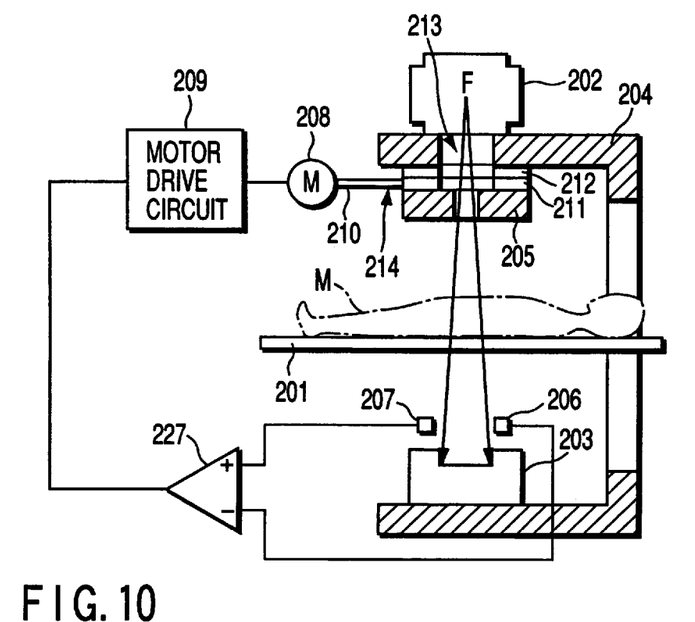
FIG. 10 is a schematic view illustrating the structure of an X-ray computed tomography apparatus according to a second embodiment of the invention.

FIG. 10 shows an essential part of an X-ray computed tomography apparatus according to a second embodiment. An X-ray tube 202 and a main X-ray detector 203 are mounted on a rotary frame 204, opposed to each other with a to-be-examined subject M on a table 1 interposed therebetween. The X-ray tube 202 has an X-ray radiation window 213 which is provided with an X-ray collimator 205 for limiting the X-ray radiation field. The X-ray collimator 205 is formed of a combination of plural slit plates. The slit plates are movable individually. The X-ray radiation field can be varied by changing the positional relationship between the slit plates and thereby changing the shapes of the slits through which an X-ray passes.

The X-ray tube 202 is formed of, for example, a rotary anode type tube, or may be formed of a fixed anode type tube. The main X-ray detector 203 consists of an arcuate ion chamber type detector with Xe gas of high pressure sealed therein, or an assembly detector that includes a scintillator for converting an X-ray into light, and a photodiode for converting light into an electric signal, or a semiconductor type detector for directly converting an X-ray into an electric signal.

A sub X-ray detector 206 for detecting the position of the X-ray radiation field is arranged at the righthand of the main X-ray detector 203 with respect to the rotation axis of the rotary frame 204. Further, a sub X-ray detector 207 for detecting the position of the X-ray radiation field is arranged at the lefthand of the main X-ray detector 203. This arrangement of the sub X-ray detectors 206 and 207 enables the detection of the shift of the X-ray radiation field in a direction parallel to the rotation axis. When the X-ray radiation field is in the home position, the output signals of the sub X-ray detectors 206 and 207 are substantially the same. On the other hand, when the X-ray radiation field has shifted from the home position as a result of the shift of the X-ray focus F due to, for example, thermal expansion, the output signals differ from each other.

The output signals of the sub X-ray detectors 206 and 207 are supplied to a differential amplifier 227 for amplifying the difference between them. The difference signal is supplied to a motor drive circuit 209 for driving a motor 208.

Figure 11:
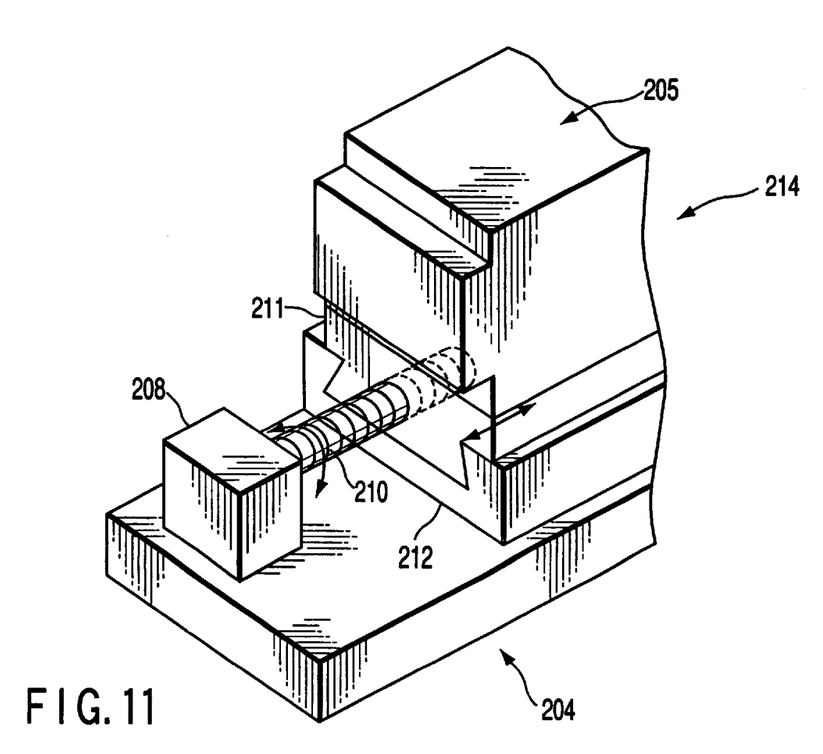
FIG. 11 is a perspective view showing a collimator shifting mechanism that appears in FIG. 10.

As is shown in FIG. 11, the drive shaft 210 of the motor 208 is associated with a slide base 211. The slice base 211 is mounted on a guide rail 212 such that it can slide in a direction parallel to the rotation axis of the rotary frame 204. The drive shaft 210 and a screw hole formed in the slide base 211 constitute a rack-and-pinion mechanism. When the drive shaft 210 rotates, the slide base 211 slides together with the X-ray collimator 205 in the direction parallel to the rotation axis of the rotary frame 204.

The operation of this embodiment will be described. Where the X-ray focus is in the home position F1, the X-ray radiation field is also in its home position on the main detector 203. Since in this state, no X-rays or the same amount of X-rays enter the sub X-ray detectors 206 and 207, the output signals of these detectors have substantially the same level. Accordingly, the output of the differential amplifier 227 is at substantially zero level. When the output of the differential amplifier 227 is at zero level, a drive circuit 209 does not drive the motor 208, and hence, the position of the collimator 205 does not change.

Figure 12:
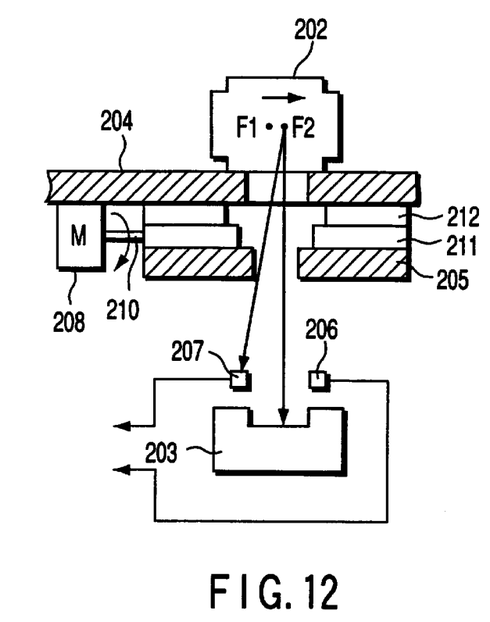
FIG. 12 is a side view showing an X-ray radiation field in the second embodiment, which corresponds to an X-ray focus shifted from a predetermined position due to thermal expansion.

On the other hand, when the X-ray focus has shifted, for example, from the home position F1 to a position F2 as a result of thermal expansion, the X-ray radiation field also shifts from the home position on the main detector 203, as is shown in FIG. 12. Since at this time, the amounts of the X-ray entering the sub X-ray detectors 206 and 207 differ from each other, the output signals of the detectors 206 and 207 differ from each other. Accordingly, the output of the differential amplifier 227 is at the level other than zero, which corresponds to the difference between the outputs of the sub X-ray detectors 206 and 207, or is at a level other than zero. Specifically, when the amount of the X-ray entering the sub X-ray detector 206 is larger than that entering the sub X-ray detector 207, the output level of the differential amplifier 227 is minus, whereas when the former is smaller than the latter, the output level of the differential amplifier 227 is plus.

Figure 13:
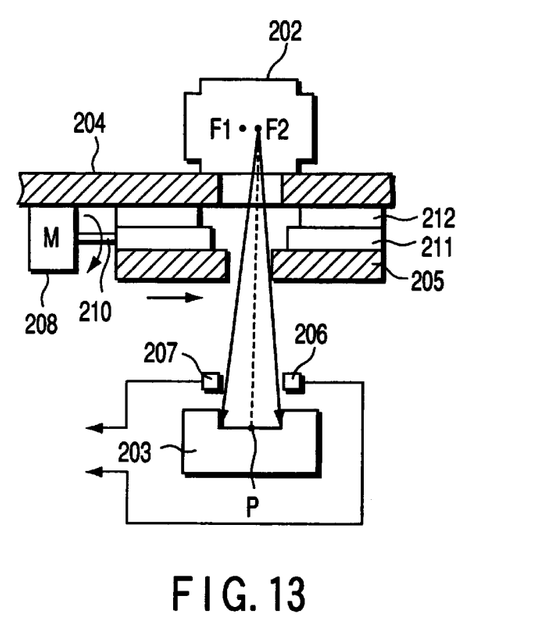
FIG. 13 is a side view illustrating an X-ray radiation field whose position is corrected by shifting the collimator in the second embodiment.

The drive circuit 209 drives the motor 208 when the output level of the differential amplifier 227 is not zero, and does not drive the motor 208 when the output level is zero. Specifically, when the output level of the differential amplifier is minus, the drive circuit 209 rotates the motor 208 in a forward direction so as to slide the X-ray collimator 205 toward the sub X-ray detector 206. On contrary, when the output level of the differential amplifier is plus, the drive circuit 209 rotates the motor 208 in a backward direction so as to slide the X-ray collimator 205 toward the sub X-ray detector 207. As a result, the X-ray radiation field returns to the home position as shown in FIG. 13.

Since the shift distance of the X-ray radiation field from the home position is indicated by the output level of the differential amplifier 227, the X-ray radiation field may be returned to the home position by adjusting the driving amount of the motor 208 by the drive circuit 209 in accordance with the output level of the differential amplifier 227.

When in the second embodiment, the x-ray radiation field has been shifted as result of, for example, the shift of the X-ray focus, it can be returned to the home position accurately in a short time. This is because the X-ray collimator is lighter than the X-ray tube or the X-ray detectors.

Third Embodiment

Figure 14:
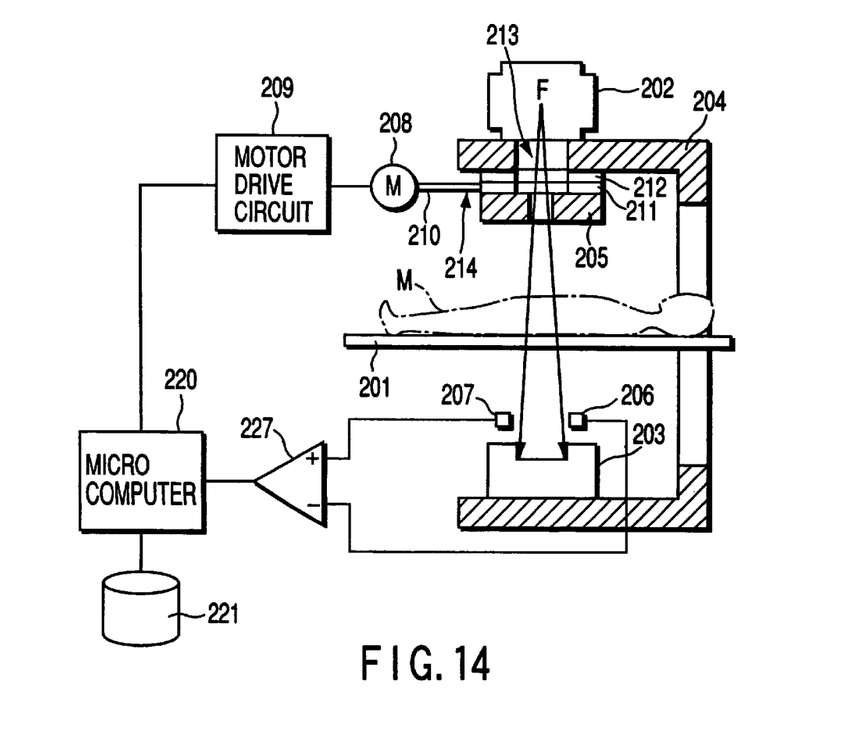
FIG. 14 is a schematic view illustrating the structure of an X-ray computed tomography apparatus according to a third embodiment of the invention.

FIG. 14 shows an essential part of an X-ray computed tomography apparatus according to a third embodiment. In FIG. 14, elements similar to those in FIG. 11 are denoted by corresponding reference numerals, and no explanation is given thereof. The apparatus of the third embodiment differs from that of the second embodiment in that the former additionally employs a microcomputer 220 for controlling the motor drive circuit 209 on the basis of the output signal of the differential amplifier 227.

The microcomputer 220 has a function for controlling the motor drive circuit 209 on the basis of the output signal of the differential amplifier 227 so as to return the X-ray radiation field to its home position, as in the second embodiment. This function works during scanning in which an X-ray is being generated.

Figure 15:
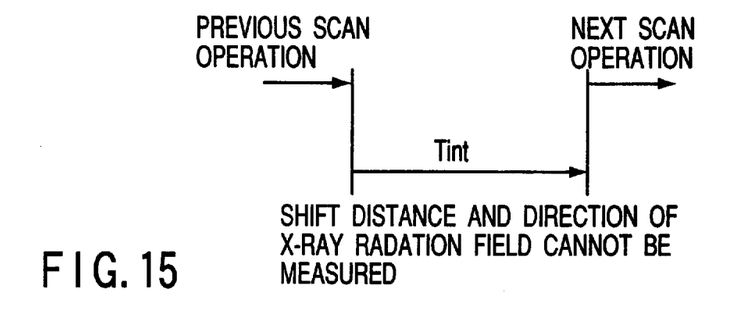
FIG. 15 is a view useful in explaining a situation assumed in the third embodiment, in which the position of the X-ray radiation field needs to be estimated.

The above function slides the X-ray collimator 205 on the basis of the output signals of the sub detectors 206 and 207, to thereby return the X-ray radiation field to the home position. Accordingly, during, for example, an interval $T_{int}$, as shown in FIG. 15, between one scan operation and another scan operation, during which no X-ray is generated (during this period, the X-ray tube 202 is cooled and the X-ray focus gradually moves toward the home position as a result of the cooling effect), the direction or the amount of the shift of the X-ray radiation field cannot be measured and hence the X-ray radiation field cannot be returned to the home position.

The microcomputer 220 has a function for estimating the amount of the direction of the shift of the X-ray radiation field while no X-ray is generated, and returning, at any time, the X-ray radiation field to the home position on the basis of the estimated direction and amount. For this function, a storage unit 221, which stores information necessary for the estimation, is provided.

Figure 16:
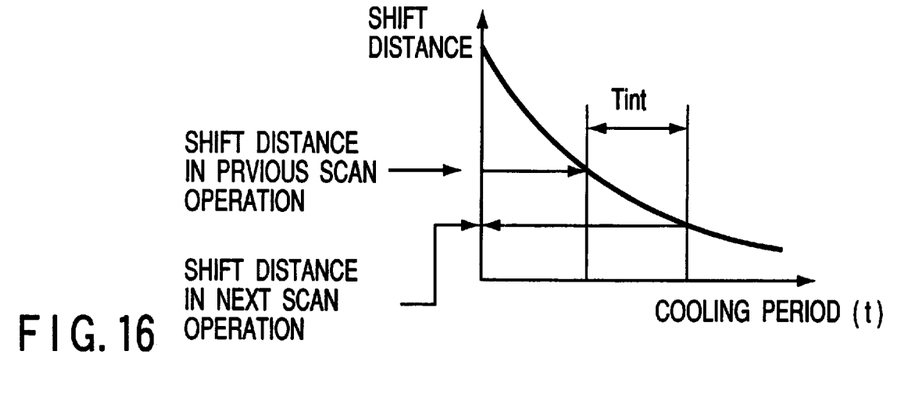
FIG. 16 is a view illustrating the relationship between the position of the X-ray radiation field and a cooling period, which is used in the third embodiment for estimating the position of the X-ray radiation field.
Figure 17:
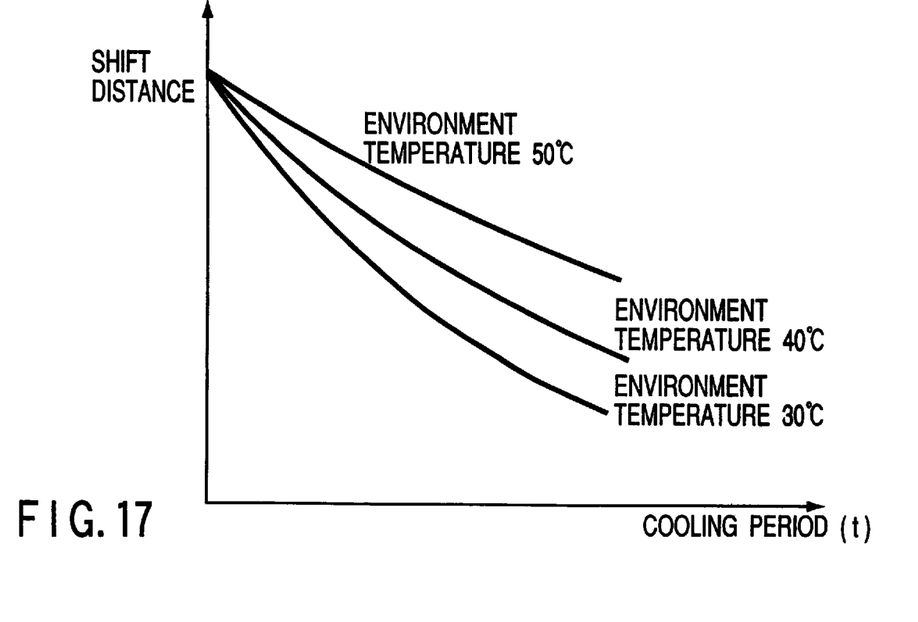
FIG. 17 is a view illustrating a state in which the relationship between the position of the X-ray radiation field and the cooling period varies in accordance with the environment temperature in the third embodiment.

The temperature of the X-ray tube 202 gradually decreases when it is cooled by oil, air or water. The time constant of the temperature decrease differs depending upon the type of the X-ray tube 202 or upon the environment temperature of the X-ray tube 202 as shown in FIG. 17. The storage unit 221 stores cooling characteristic data (time constants) as shown in FIG. 16.

The microcomputer 220 can calculate, from cooling characteristic data, the distance through which the X-ray radiation field shifts, as a result of the cooling effect, from the termination of the previous scan operation to the present time. The microcomputer 220 controls the drive circuit 209 to drive the X-ray collimator 205 so as to return the X-ray radiation field by the shift distance.

As a result, the X-ray radiation field can be set in the home position even when no X-ray is generated. In other words, at the start of the next scan operation, it is not necessary to radiate an X-ray so as to measure the shift distance of the X-ray radiation field for setting the X-ray radiation field in the home position.

Although in each of the above-described embodiments, the X-ray collimator 205 is moved, a so-called beam trimmer provided over the X-ray detector 203, aligned across the path of the X-ray, may be moved instead of the collimator. Also in this case, the same advantage as above can be obtained. Alternatively, both the X-ray collimator 205 and the beam trimmer may be moved. This structure enables more accurate focus correction.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
   an X-ray tube for generating an X-ray;
   a main X-ray detector opposed to the X-ray tube with a to-be-examined subject interposed therebetween, the main X-ray detector detecting an X-ray having passed through the to-be-examined subject, the main X-ray detector having a plurality of main detector element arrays arranged parallel to each other in a slice direction, each of the plurality of main detector element arrays having a plurality of main detector elements arrayed in a channel direction;
   a first sub X-ray detector opposed to the X-ray tube for directly detecting an X-ray emitted from the X-ray tube, the first sub X-ray detector arranged at a righthand of the main X-ray detector in the channel direction and having at least one first sub detector element; and
   a second sub X-ray detector opposed to the X-ray tube for directly detecting an X-ray emitted from the X-ray tube, the second sub X-ray detector arranged at a lefthand of the main X-ray detector in the channel direction and having at least one second sub detector element.

2. An X-ray computed tomography apparatus according to claim 1, further comprising:
   a correction unit for correcting a projection data set output from the main X-ray detector on the basis of an output of the first sub X-ray detector and an output of the second sub X-ray detector; and
   a reconstruction unit for reconstructing tomogram data on the basis of the corrected projection data set.

3. An X-ray computed tomography apparatus according to claim 1, further comprising a unit for detecting, on the basis of an output of the first sub X-ray detector and an output of the second sub X-ray detector, a channel-directional shift of a radiation field of the X-ray, and at least one of a slice-directional shift of the radiation field of the X-ray and a slant of the radiation field of the X-ray.

4. An X-ray computed tomography apparatus according to claim 1, wherein the first sub X-ray detector has a plurality of first sub detector elements arrayed in the slice direction.

5. An X-ray computed tomography apparatus according to claim 1, wherein the second sub X-ray detector has a plurality of second sub detector elements arrayed in the slice direction.

6. An X-ray computed tomography apparatus according to claim 1, wherein:
   the first sub X-ray detector has a plurality of first sub detector elements arrayed in the slice direction; and
   the second sub X-ray detector has a plurality of second sub detector elements arrayed in the slice direction.

7. An X-ray computed tomography apparatus according to claim 1, wherein:
   the first sub X-ray detector has a plurality of first sub detector elements arrayed in the slice direction, and an entire width of the arrayed first sub detector elements is wider than an entire width of the main detector element arrays arranged parallel to each other; and
   the second sub X-ray detector has a plurality of second sub detector elements arrayed in the slice direction, and an entire width of the arrayed second sub detector elements is wider than an entire width of the main detector element arrays arranged parallel to each other.

8. An X-ray computed tomography apparatus according to claim 1, wherein the first sub X-ray detector has a sensitivity that is lower at a slice-directional central portion thereof than at slice-directional peripheral portions thereof, and the second sub X-ray detector has a sensitivity that is lower at a slice-directional central portion thereof than at slice-directional peripheral portions thereof.

9. An X-ray computed tomography apparatus according to claim 1, wherein:
the first sub X-ray detector has a plurality of first sub detector elements arrayed in the slice direction, those of the first sub detector elements which are located in a slice-directional central area of the first sub X-ray detector having a thickness thinner than those of the first sub detector elements which are located in slice-directional peripheral areas of the first sub X-ray detector; and
the second sub X-ray detector has a plurality of second sub detector elements arrayed in the slice direction, those of the second sub detector elements which are located in a slice-directional central area of the second sub X-ray detector having a thickness thinner than those of the second sub detector elements which are located in slice-directional peripheral areas of the second sub X-ray detector.

10. An X-ray computed tomography apparatus according to claim 1, wherein X-ray filters are arranged at slice-directional central portions of the first and second sub X-ray detectors and their vicinities.

11. An X-ray computed tomography apparatus according to claim 1, wherein:
the first sub X-ray detector has a plurality of first sub detector elements arrayed in the slice direction, each of the first sub detector elements being formed of a scintillator and a photodiode, an optical filter being inserted between the scintillator and the photodiode of each of those of the first sub detector elements, which are arranged in a slice-directionally central area and its vicinity of the first sub X-ray detector; and
the second sub X-ray detector has a plurality of second sub detector elements arrayed in the slice direction, each of the second sub detector elements being formed of a scintillator and a photodiode, an optical filter being inserted between the scintillator and the photodiode of each of those of the second sub detector elements, which are arranged in a slice-directional central area and its vicinity of the second. sub X-ray detector.

12. An X-ray computed tomography apparatus according to claim 1, wherein the first and second sub X-ray detectors are in contact with the main X-ray detector.

13. An X-ray computed tomography apparatus according to claim 1, wherein the first and second sub X-ray detectors are separated by a predetermined distance from the main X-ray detector.

14. An X-ray computed tomography apparatus comprising:
an X-ray tube for generating an X-ray;
a main X-ray detector opposed to the X-ray tube with a to-be-examined subject interposed therebetween, the main X-ray detector detecting an X-ray having passed through the to-be-examined subject, the main X-ray detector having a plurality of main detector elements arrayed in a channel direction;
a first sub X-ray detector opposed to the X-ray tube for directly detecting an X-ray emitted from the X-ray tube, the first sub X-ray detector arranged at a righthand of the main X-ray detector in the channel direction and having at least one first sub detector element; and
a second sub X-ray detector opposed to the X-ray tube for directly detecting an X-ray emitted from the X-ray tube, the second sub X-ray detector arranged at a lefthand of the main X-ray detector in the channel direction and having at least one second sub detector element.

15. An X-ray computed tomography apparatus comprising:
an X-ray tube for generating an X-ray;
a main X-ray detector opposed to the X-ray tube with a to-be-examined subject interposed therebetween, the main X-ray detector detecting an X-ray having passed through the to-be-examined subject, the main X-ray detector having a plurality of main detector elements arrayed in a channel direction;
a first sub X-ray detector opposed to the X-ray tube for directly detecting an X-ray emitted from the X-ray tube, the first sub X-ray detector arranged at a righthand of the main X-ray detector in the channel direction;
a second sub X-ray detector opposed to the X-ray tube for directly detecting an X-ray emitted from the X-ray tube, the second sub X-ray detector arranged at a lefthand of the main X-ray detector in the channel direction;
a reconstruction unit for reconstructing tomogram data on the basis of a projection data set output from the main X-ray detector;
an X-ray collimator interposed between the X-ray tube and the to-be-examined subject;
a slide mechanism which mounts thereon the X-ray collimator such that the X-ray collimator can slide in a direction substantially parallel to the channel direction; and
a drive circuit for driving the slide mechanism on the basis of an output of the first sub X-ray detector and an output of the second sub X-ray detector, in order to slide the X-ray collimator.

16. An X-ray computed tomography apparatus according to claim 15, wherein the drive circuit drives the slide mechanism to slide the X-ray collimator when the difference between the output of the first sub X-ray detector and the output of the second sub X-ray detector is not substantially zero, and does not drive the slide mechanism for sliding the X-ray collimator when the difference between the output of the first sub X-ray detector and the output of the second sub X-ray detector is substantially zero.

17. An X-ray computed tomography apparatus according to claim 15, further comprising means for generating a difference signal indicative of the difference between the output of the first sub X-ray detector and the output of the second sub X-ray detector, and wherein the drive circuit drives the slide mechanism on the basis of the difference signal.

18. An X-ray computed tomography apparatus according to claim 15, wherein the drive circuit drives the slide mechanism until the difference between the output of the first sub X-ray detector and the output of the second sub X-ray detector becomes substantially zero.

19. An X-ray computed tomography apparatus according to claim 15, further comprising a computer for controlling the drive circuit so as to slide the X-ray collimator by a distance corresponding to a time having passed after the generation of the X-ray stops.

20. An X-ray computed tomography apparatus according to claim 15, further comprising a storage unit for storing information indicative of the relationship between a time having passed after the generation of the X-ray stops, and a distance through which an X-ray radiation field shifts; and a computer for controlling the drive circuit so as to slide the X-ray collimator by the shift distance of the X-ray radiation field corresponding to the time having passed after the generation of the X-ray stops.

21. An X-ray computed tomography apparatus comprising:

an X-ray tube for generating an X-ray;

a main X-ray detector opposed to the X-ray tube with a to-be-examined subject interposed therebetween, the main X-ray detector detecting an X-ray having passed through the to-be-examined subject, the main X-ray detector having a plurality of main detector element arrays arranged parallel to each other in a slice direction, each of the plurality of main detector element arrays having a plurality of main detector elements arrayed in a channel direction; and a sub X-ray detector for two-dimensionally detecting the position of a radiation field of the X-ray entering the main X-ray detector.

* * * * *